United States Patent
Fischer et al.

(10) Patent No.: US 6,175,019 B1
(45) Date of Patent: Jan. 16, 2001

(54) PROCESS FOR THE PREPARATION OF 1,3-DIMETHYLIMIDAZOLIUM 4-CARBOXYLATE

(75) Inventors: Jakob Fischer, Kirchdorf; Wolfgang Siegel, Limburgerhof; Volker Bomm, Mutterstadt; Martin Fischer, Ludwigshaften; Klaus Mundinger, Limburgerhof, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/372,063

(22) Filed: Aug. 11, 1999

(30) Foreign Application Priority Data

Aug. 12, 1998 (DE) .............................. 198 36 477

(51) Int. Cl.[7] .................................................. C07D 233/90
(52) U.S. Cl. ............................................. 548/334.5
(58) Field of Search ........................................ 548/334.5

(56) References Cited

U.S. PATENT DOCUMENTS 5,856,513  1/1999  Ue et al. .............................. 548/347

FOREIGN PATENT DOCUMENTS 291 074   11/1988  (EP) .

OTHER PUBLICATIONS

Tetrahedron Lett. 38, 3883–4 (1997).
Tetrahedron 29, (1973) 3135–6.
OZ 49266 = German 198 364 74.1.
Synthesis, 382–3 (1986).
Liebigs Ann. Chem. 1987 77–79.
JP Abstr. 128:167423p.
JP Abstr. 128:167424q.

*Primary Examiner*—Mukund J. Shah
*Assistant Examiner*—Hong Liu
(74) *Attorney, Agent, or Firm*—Keil & Weinkauf

(57) ABSTRACT

1,3-Dimethylimidazolium 4-carboxylate is prepared by reacting 1-methylimidazole with dimethyl carbonate optionally in the presence of a solvent in accordance with the following reaction scheme:

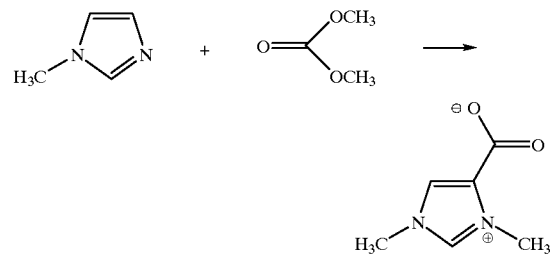

19 Claims, No Drawings

PROCESS FOR THE PREPARATION OF 1,3-DIMETHYLIMIDAZOLIUM 4-CARBOXYLATE

Process for the preparation of 1,3-dimethylimidazolium 4-carboxylate

The present invention relates to a process for the preparation of 1,3-dimethylimidazolium 4-carboxylate.

1,3-dimethylimidazolium 4-carboxylate is used, according to the parallel German Application No. 198 364 74.1, as catalyst in the preparation of isophoronenitrile (IPN) from isophorone and hydrogen cyanide.

1,3-dimethylimidazolium 4-carboxylate, a betaine of the formula I

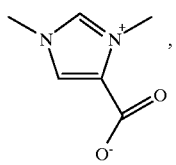

(I)

is a natural substance and is known under the name norzooanemonin, the isolation and characterization of which has been described in Tetrahedron Lett. 38, (1997) 3883-4.

In Tetrahedron 29, (1973) 3135-6, 1,3-dimethylimidazolium 4-carboxylate is prepared by reacting imidazole-4-carboxylic acid with dimethyl sulfate. A disadvantage of this process is the requisite handling of the highly toxic dimethyl sulfate.

It is an object of the present invention to find an alternative economical process for the preparation of 1,3-dimethylimidazolium 4-carboxylate.

We have found that this object is achieved by a process for the preparation of 1,3-dimethylimidazolium 4-carboxylate which involves reacting 1-methylimidazole with dimethyl carbonate.

From EP-A-291 074, it is known that dimethyl carbonate acts as a methylating agent during its reaction with an approximately stoichiometric amount of a tertiary amine. Thus, for example, the reaction of triethylamine with dimethyl carbonate gives the product triethylmethylammonium methyl carbonate in 89.9% yield (loc. cit., Example 1).

Synthesis, (1986) 382-3 and Liebigs Ann. Chem., (1987), 77-9 describe the synthesis of 1-methylimidazole in 91% yield by reacting imidazole with dimethyl carbonate in the presence of a catalyst. According to Liebigs Ann. Chem. (1987), page 77, 2nd column, 4th paragraph, the missing 9% yield can be attributed to unreacted imidazole. This publication also teaches that an attack by the imidazole or the 1-methylimidazole on the carbonyl group of the dimethyl carbonate does not take place.

Furthermore, from JP-A-10 17,553 (Chem. Abstracts 128: 167423p) and from JP-A-10 17,554 (Chem. Abstracts 128: 167424q), it is known that N-alkylimidazolines are methylated by reaction with dimethyl carbonate on the nitrogen atom in the 3-position. Thus, the reaction of 1-ethyl-2-methylimidazoline with $(MeO)_2CO$ gives the product 1-ethyl-2,3-dimethylimidazolinium methyl carbonate in 98% yield.

In the light of the documents cited above, it was to be expected that the reaction of 1-methylimidazole with dimethyl carbonate would give the product 1,3-dimethylimidazolium methyl carbonate in accordance with the equation below.

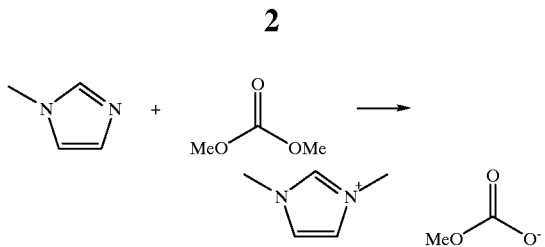

However, it has surprisingly been found that the reaction of 1-methylimidazole with dimethyl carbonate leads to 1,3-dimethylimidazolium 4-carboxylate of the formula I in high yields:

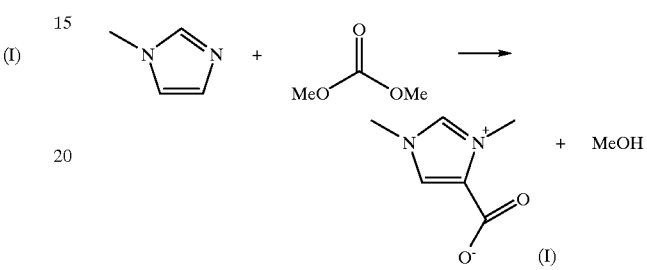

The novel process can be carried out as follows.

In general, 1-methylimidazole is initially introduced together with from 0.1 to 2 mole equivalents, preferably from 0.5 to 1.5 mole equivalents, particularly preferably from 0.9 to 1.1 mole equivalents, very particularly preferably 1 mole equivalent, of dimethyl carbonate, with or without a solvent, and the mixture is then heated to from 50 to 200° C., preferably from 100 to 180° C. with stirring.

In a preferred embodiment, the 1-methylimidazole is initially introduced, with or without a solvent, into the reaction vessel and is heated to from 50 to 200° C, preferably from 100 to 180° C., and to this is then added from 0.5 to 1.5 mole equivalents, preferably from 0.9 to 1.1 mole equivalents, particularly preferably one mole equivalent, of dimethyl carbonate.

Examples of suitable solvents are aliphatic or aromatic solvents, such as pentane, hexane, benzene, toluene, xylene, ethers, such as methyl tert-butyl ether, diethyl ether, tetrahydrofuran, dioxane, amides, such as dimethylformamide, dimethylacetamide, N-methylpyrrolidone, ureas, such as N,N'-dimethylethyleneurea, N,N'-dimethylpropyleneurea and N,N,N',N'-tetra-n-butylurea, or additional dimethyl carbonate.

The reaction is particularly preferably carried out in the absence of a solvent.

The reaction times generally depend on the reaction temperature; the higher the chosen reaction temperature, the shorter is the reaction time. The reaction times are generally from 5 hours to 3 days, preferably from 12 to 24 hours.

The reaction is generally carried out at a pressure (measured in absolute terms) of from 0.05 to 5 MPa, preferably from 0.1 to 1 MPa. The reaction is particularly preferably carried out in a closed reaction vessel under autogenous pressure.

The reaction can be carried out either continuously or batchwise in common reaction vessels or reactors, such as stirred reactors, tubular reactors, battery of stirred containers.

The reaction product I is expediently purified by crystallization. Suitable solvents for this purpose are alcohols, such as methanol, ethanol, propanol, ethers, such as methyl tert-butyl ether, diethyl ether, tetrahydrofuran, dioxane, ketones, such as acetone, diethyl ketone, and esters, such as ethyl acetate.

EXAMPLE

Preparation of 1,3-dimethylimidazolium 4-carboxylate (norzooanemonin)

An autoclave was charged with 0.9 mol (73.8 g) of 1-methylimidazole and 0.9 mol (81.0 g) of dimethyl carbonate at room temperature. The mixture was then heated to 140° C. and stirred at this temperature for 20 hours (autogenous pressure: about 0.5 MPa). Cooling to room temperature resulted in a thick yellow suspension. The crystals were filtered off and dried in an oil pump vacuum. Crude weight: 119.4 g (=94.7% crude yield).

The crystals were recrystallized from an ethanol/methanol mixture (approximately 1:1). This produced white crystals, which were filtered off and dried under a high vacuum. Weight: 48.9 g.

The mother liquor was evaporated to dryness. The yellow-oily residue which remained was again taken up in a hot 1:1 ethanol/methanol mixture and precipitated at low temperature. This gave a further 53.9 g of product.

Total yield: 102.8 g (81.5%)

Characterization of the product:

Melting point: 240° C. (Decomposition).

MS (electron spray ionization ESI, direct inlet): M=141 $(M+H)^+$.

Elemental analysis: calculated: C 51.4; H 5.8; N 20.0; O 22.8 $C_6H_8N_2O_2$; MW=140.14 found: C 51.3; H 5.7; N 19.9; O 23.4.

$^1$H-NMR (400 MHz, $D_2O$) δ (ppm)=3.98 (3 H); 4.12 (3H); 7.88 (1H); 1 H exchanges in $D_2O$.

$^{13}$C-NMR (100.61 MHz, $D_2O$) δ (ppm)=38.55 (methyl); 38.65 (methyl); 129.03 (CH); 133.59 (C—$COO^-$); 140.82 (t, C-D coupling); 165.8 ($COO^-$).

IR (KBr), [$cm^{-1}$]: 3451 ss, 1621 ss,

We claim:

1. The process for the preparation of 1,3-dimethylimidazolium 4-carboxylate, which comprises reacting 1-methylimidazole with dimethyl carbonate.

2. The process of claim 1, wherein 1-methylimidazole is reacted with from 0.5 to 1.5 mole equivalents of dimethyl carbonate.

3. The process of claim 1, wherein the reaction is carried out at from 50 to 200° C.

4. The process of claim 1, wherein the reaction is carried out in the absence of a solvent.

5. The process of claim 3, wherein the reaction is carried out in the absence of a solvent.

6. The process of claim 3, wherein the reaction is carried out at a pressure of from 0.05 to 5 MPa.

7. The process of claim 5, wherein the reaction is carried out at a pressure of from 0.05 to 5 MPa.

8. The process of claim 3, wherein the reaction is carried out in a closed reaction vessel at autogeneous pressure.

9. The process of claim 1, wherein 1-methylimidazole is reacted with from 0.9 to 1.1 mole equivalents of dimethyl carbonate.

10. The process of claim 1, wherein the reaction is carried out at from 100 to 180° C.

11. The process of claim 1, wherein the reaction is carried out at a pressure of from 0.05 to 5 MPa.

12. The process of claim 1, wherein the reaction is carried out at a pressure of from 0.1 to 1 MPa.

13. The process of claim 1, wherein the reaction is carried out in the presence of a solvent.

14. The process of claim 13, wherein the solvent is selected from the group consisting of aliphatic and aromatic hydrocarbons, ethers, amides, ureas and dimethyl carbonate.

15. The process of claim 13, wherein the solvent is selected from the group consisting of pentane, hexane, benzene, toluene, xylene, methyl tert.-butyl ether, diethyl ether, tetrahydrofuran, diox-ane, dimethylformamide, dimethylacetamide, N-methylpyrrolidone, N,N'-dimethylethyleneurea, N,N'-diemthylpropyleneurea, N,N,N', N'-tetra-n-butylurea and dimethyl carbonate.

16. The process of claim 13, wherein the reaction is carried out at from 50 to 200° C.

17. The process of claim 16, wherein the reaction is carried out at a pressure of from 0.05 to 5 MPa.

18. The process of claim 16, wherein the reaction is carried out at a pressure of from 0.1 to 1 MPa.

19. The process of claim 16, wherein the reaction is carried out in a closed reaction vessel at autogeneous pressure.

* * * * *

UNITED STATES PATENT AND TRADEMARK OFFICE
CERTIFICATE OF CORRECTION

PATENT NO.: 6,175,019

DATED: January 16, 2001

INVENTOR(S): FISCHER et al.

It is certified that error appears in the above-identified patent and that said Letters Patent is hereby corrected as shown below:

Col. 4, claim 15, line 34, "N,N'-diemthylpropyleneurea" should be --N,N'-dimethylpropyleneurea--.

Signed and Sealed this

Twenty-ninth Day of May, 2001

Attest:

NICHOLAS P. GODICI

*Attesting Officer*           *Acting Director of the United States Patent and Trademark Office*